US009365902B2

(12) United States Patent
Huang et al.

(10) Patent No.: US 9,365,902 B2
(45) Date of Patent: Jun. 14, 2016

(54) DETECTION OF BISULFITE CONVERTED NUCLEOTIDE SEQUENCES

(71) Applicant: Abbott Molecular Inc., Des Plaines, IL (US)

(72) Inventors: Shihai X. Huang, Lincolnshire, IL (US); Edward N. Granados, Vernon Hills, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 97 days.

(21) Appl. No.: 14/186,352

(22) Filed: Feb. 21, 2014

(65) Prior Publication Data

US 2014/0287404 A1 Sep. 25, 2014

Related U.S. Application Data

(60) Provisional application No. 61/798,520, filed on Mar. 15, 2013.

(51) Int. Cl.
*C07H 21/04* (2006.01)
*C12Q 1/68* (2006.01)
*C12P 19/34* (2006.01)

(52) U.S. Cl.
CPC ........ *C12Q 1/6886* (2013.01); *C12Q 2600/154* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,800,195 A | 1/1989 | Burgess et al. |
| 4,851,331 A | 7/1989 | Vary et al. |
| 4,965,188 A | 10/1990 | Mullis et al. |
| 5,137,806 A | 8/1992 | LeMaistre et al. |
| 5,310,652 A | 5/1994 | Gelfand et al. |
| 5,322,770 A | 6/1994 | Gelfand |
| 5,539,082 A | 7/1996 | Nielsen et al. |
| 5,561,058 A | 10/1996 | Gelfand et al. |
| 5,595,890 A | 1/1997 | Newton et al. |
| 5,639,611 A | 6/1997 | Wallace et al. |
| 5,641,864 A | 6/1997 | Gelfand |
| 5,693,517 A | 12/1997 | Gelfand et al. |
| 5,786,146 A | 7/1998 | Herman et al. |
| 5,849,497 A | 12/1998 | Steinman |
| 5,994,056 A | 11/1999 | Higuchi |
| 7,620,386 B2 | 11/2009 | Wood et al. |
| 7,820,386 B2 | 10/2010 | Lai |
| 2004/0014105 A1 | 1/2004 | Schroeder et al. |
| 2005/0227257 A1 | 10/2005 | Abravaya et al. |
| 2006/0134643 A1 | 6/2006 | Berlin et al. |
| 2009/0317810 A1 | 12/2009 | Lofton-Day et al. |
| 2011/0009277 A1 | 1/2011 | Devos et al. |

FOREIGN PATENT DOCUMENTS

| | | | |
|---|---|---|---|
| EP | 0487218 A1 | 5/1992 | |
| EP | 0512334 A2 | 11/1992 | |
| WO | WO-9220702 A1 | 11/1992 | |
| WO | WO-9220703 A1 | 11/1992 | |
| WO | WO-9322456 A1 | 11/1993 | |
| WO | 2005061734 A3 | 7/2005 | |
| WO | WO 2008149237 A2 * | 12/2008 | ........... C12Q 1/6806 |

OTHER PUBLICATIONS

Fukushige, et al. "DNA Methylation in Cancer: A Gene Silencing Mechanism and the Clinical Potential of Its Biomarkers" J. Exp. Med.; 2013; vol. 229; pp. 173-185.
Nollau, et al. "Methods for detection of point mutations: performance and quality assessment" Clinical Chemistry; 1997; vol. 43; No. 7, pp. 1114-1128.
Grunau, et al. "Bisulfite genomic sequencing: systematic investigation of critical experimental parameters" Nucleic Acids Research; 2001; vol. 29; No. 13; pp. 1-7.
Toth, et al. "The Influence of Methylated Septin 9 Gene on RNA and Protein Level in Colorectal Cancer" Pathol. Oncol. Res.; 2001; vol. 17; pp. 503-509.
Heichman "Septin 9 (SEPT9) Methylated DNA Detection by Real-Time PCR" ARUP Laboratories; National Reference Library; Jan. 2012; 2 pages.
Hersberger, et al., "Rapid detection of the CYP2D*3, CYP2D6*4, and CYP2D6*6 alleles by tetra-primer PCR and of the CYP2D6*5 allele by multiplex long PCR" Clinical Chemistry; Jan. 10, 2000; vol. 46; No. 8; pp. 1072-1077.
Abramson R.D., et al., "Nucleic Acid Amplification Technologies," Current Opinion in Biotechnology, 1993, vol. 4 (1), pp. 41-47.
Baba Y., et al., "Negative Lymph-node Count is Associated with Survival in Patients with Resected Esophageal Squamous Cell Carcinoma," Surgery, 2013, vol. 153 (2), pp. 234-241.
Dagdemir A., et al., "Breast Cancer. Mechanisms Involved in Action of Phytoestrogens and Epigenetic Changes," In Vivo, 2013, vol. 27 (1), pp. 1-9.
Devos T., et al., "Circulating Methylated SEPT9 DNA in Plasma is a Biomarker for Colorectal Cancer," Clinical Chemistry, 2009, vol. 55 (7), pp. 1337-1346.
Egholm M., et al., "PNA Hybridizes to Complementary Oligonucleotides Obeying the Watson-Crick Hydrogen-Bonding Rules," Nature, 1993, vol. 365 (6446), pp. 566-568.
El-Maarri O., "Methods: Dna Methylation," Advances in Experimental Medicine and Biology, 2003, vol. 544, pp. 197-220.
Erlich H.A., Ed., PCR Technology: Principles and Applications for DNA Amplification, W.H. Freeman and Company, 1992, Tables of Contents.
Fraga M.F., et al., "DNA Methylation: A Profile of Methods and Applications," Biotechniques, 2002, vol. 33 (3), pp. 632, 634, 636-649.
Frommer M., et al., "A Genomic Sequencing Protocol that Yields a Positive Display of 5-Methylcytosine Residues in Individual DNA Strands," Proceedings of the National Academy of Sciences, 1992, vol. 89 (5), pp. 1827-1831.

(Continued)

*Primary Examiner* — Young J Kim
(74) *Attorney, Agent, or Firm* — Pierce Atwood LLP; Kevin M. Farrell; David J. Wilson

(57) ABSTRACT

The invention is to improved compositions and methods for the detection of target bisulfite converted methylated nucleotide sequences.

2 Claims, 3 Drawing Sheets

(56) References Cited

OTHER PUBLICATIONS

Furst R.W., et al., "A Differentially Methylated Single CpG-Site is Correlated with Estrogen Receptor Alpha Transcription," Journal of Steroid Biochemistry and Molecular Biology, 2012, vol. 130 (1-2), pp. 96-104.
Gasche J.A., et al., "Epigenetic Mechanisms in Oral Carcinogenesis," Future Oncology, 2012, vol. 8 (11), pp. 1407-1425.
Gonzalgo M.L., et al., "Rapid Quantitation of Methylation Differences at Specific Sites Using Methylation-Sensitive Single Nucleotide Primer Extension (Ms-SNuPE)," Nucleic Acids Research, 1997, vol. 25 (12), pp. 2529-2531.
Grutzmann R., et al., "Sensitive Detection of Colorectal Cancer in Peripheral Blood by Septin 9 DNA Methylation Assay," PLoS One, 2008, vol. 3 (11), p. e3759.
Hancock D.K., et al., "Design and Use of a Peptide Nucleic Acid for Detection of the Heteroplasmic Low-Frequency Mitochondrial Encephalomyopathy, Lactic Acidosis, and Stroke-Like Episodes (MELAS) Mutation in Human Mitochondrial DNA," Clinical Chemistry, 2002, vol. 48 (12), pp. 2155-2163.
Hanvey J.C., et al., "Antisense and Antigene Properties of Peptide Nucleic Acids," Science, 1992, vol. 258 (5087), pp. 1481-1485.
Herman J.G., et al., "Methylation-Specific PCR: A Novel PCR Assay for Methylation Status of Cpg Islands," Proceedings of the National Academy of Sciences, 1996, vol. 93 (18), pp. 9821-9826.
Hyrup B., "Peptide Nucleic Acids (PNA): Synthesis, Properties and Potential Applications," Bioorganic and Medicinal Chemistry, 1996, vol. 4 (1), pp. 5-23.
Innis M.A., et al., PCR Protocols—A Guide to Methods and Applications, Academic Press Inc., 1990, Table of Contents.
International Search Report and Written Opinion for Application No. PCT/US14/17633, mailed on May 19, 2014, 9 pages.
Karadag A., et al., "A Novel Technique Based on a PNA Hybridization Probe and FRET Principle for Quantification of Mutant Genotype in Fibrous Dysplasia/Mccune-Albright Syndrome," Nucleic Acids Research, 2004, vol. 32 (7), p. e63.
Kirishima T., et al., "Detection of YMDD Mutant Using a Novel Sensitive Method in Chronic Liver Disease Type B Patients Before and During Lamivudine Treatment," Journal of Hepatology, 2002, vol. 37 (2), pp. 259-265.
Kobayashi M., et al., "Fluorescence-Based DNA Minisequence Analysis for Detection of Known Single-Base Changes in Genomic DNA," Molecular and Cellular Probes, 1995, vol. 9 (3), pp. 175-182.
Kyger E.M., et al., "Detection of the Hereditary Hemochromatosis Gene Mutation by Real-Time Fluorescence Polymerase Chain Reaction and Peptide Nucleic Acid Clamping," Analytical Biochemistry, 1998, vol. 260 (2), pp. 142-148.
Laird P.W., "The Power and the Promise of DNA Methylation Markers," Nature Reviews. Cancer, 2003, vol. 3 (4), pp. 253-266.
Lazar J.G., "Advanced Methods in PCR Product Detection," PCR Methods and Applications, 1994, vol. 4 (1), pp. S1-S14.
Nielsen P.E., "Sequence-selective Recognition of DNA by Strand Displacement with a Thymine-substituted Polyamide," Science, 1991, vol. 254 (5037), pp. 1497-1500.
Ohishi W., et al., "Identification of Rare Polymerase Variants of Hepatitis B Virus Using a Two-Stage PCR with Peptide Nucleic Acid Clamping," Journal of Medical Virology, 2004, vol. 72 (4), pp. 558-565.
Orita M., et al., "Detection of Polymorphisms of Human DNA by Gel Electrophoresis as Single-Strand Conformation Polymorphisms," Proceedings of the National Academy of Sciences, 1989, vol. 86 (8), pp. 2766-2770.
Orum H., et al., "Single Base Pair Mutation Analysis by PNA Directed PCR Clamping," Nucleic Acids Research, 1993, vol. 21 (23), pp. 5332-5336.
Paul C.L., et al., "Cytosine Methylation: Quantitation by Automated Genomic Sequencing and Genescan Analysis," BioTechniques, 1998, vol. 21(20), pp. 126-133.
Sambrook J., et al., eds., Molecular Cloning: A Laboratory Manual, 3rd Edition, Cold Spring Harbor Laboratory, 2001, Table of Contents.
Sun X., et al., "Detection of Tumor Mutations in the Presence of Excess Amounts of Normal DNA," Nature Biotechnology, 2002, vol. 20 (2), pp. 186-189.
Taback B., et al., "Peptide Nucleic Acid Clamp PCR: A Novel K-Ras D Mutation Detection Assay for Colorectal Cancer Micrometastases in Lymph Nodes," 2004, vol. 111 (3), pp. 409-414.
Takiya T., et al., "An Empirical Approach for Thermal Stability (Tm) Prediction of PNA/DNA Duplexes," Nucleic Acids Symposium Series, 2004, vol. 48, pp. 131-132.
Takiya T., et al., "Identification of Single Base-pair Mutation on uidA Gene of *Escherichia coli* O157:H7 by Peptide Nucleic Acids (PNA) Mediated PCR Clamping," Bioscience, Biotechnology and Biochemistry, 2004, vol. 68 (2), pp. 360-368.
Thiede C., et al., "Simple and Sensitive Detection of Mutations in the Ras Proto-Oncogenes Using PNA-Mediated PCR Clamping," 1996, vol. 24 (5), pp. 983-984.
Versteeg R., "Aberrant Methylation in Cancer," American Journal of Human Genetics, 1997, vol. 60 (4), pp. 751-754.
Warren J.D., et al., "Septin 9 Methylated DNA is a Sensitive and Specific Blood Test for Colorectal Cancer," BMC Medicine, 2011, vol. 9, pp. 133.
Willard S.S., et al., "Regulators of Gene Expression as Biomarkers for Prostate Cancer," American Journal of Cancer Research, 2012, vol. 2 (6), pp. 620-657.
Aldige, et al. "First Transatlantic Symposium on Strategies to Increase Colorectal Cancer Screening and Save More Lives" Transatlantic Symposium; Felix Burda Foundation; Apr. 20, 2009 (4 pages).
Yim R.L., et al., "DNA Methylation of Tumor Suppressive miRNAs in Non-Hodgkin's Lymphomas," Frontiers in Genetics, 2012, vol. 3 (233), 8 pages.

* cited by examiner

SEQUENCE LISTING

```
<160> NUMBER OF SEQ ID NOS: 33

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
```

-continued

```
      primer
<220> FEATURE:
<221> NAME/KEY: modified_base
<222> LOCATION: (5)..(5)
<223> OTHER INFORMATION: Any abasic nucleotide

<400> SEQUENCE: 1
gattngttgt ttattagtta ttatgt                                              26

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaataatccc atccaact                                                      18

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gttattatgt tggattttgt ggttaatgtg tag                                     33

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
ttaaccgcga aatccgac                                                      18

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tccaactaca cattaaccac aaaatcc                                            27

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
catccaacta cacattaacc acaaaatc                                           28

<210> SEQ ID NO 7
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 7
tatgttggat tttgtgg                                                    17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ccaactacac attaacc                                                    17

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (19)..(19)
<223> OTHER INFORMATION: BHQ1-dT

<400> SEQUENCE: 9
cggatttcgc ggttaacgt                                                  19

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (4)..(4)
<223> OTHER INFORMATION: 5-Propynyl dU
<220> FEATURE:
<221> NAME/KEY: modified_base
<222> LOCATION: (7)..(7)
<223> OTHER INFORMATION: 5-Propynyl dU
<220> FEATURE:
<221> NAME/KEY: modified_base
<222> LOCATION: (10)..(10)
<223> OTHER INFORMATION: 5-Propynyl dU
<220> FEATURE:
<221> NAME/KEY: modified_base
<222> LOCATION: (12)..(13)
<223> OTHER INFORMATION: 5-Propynyl dU

<400> SEQUENCE: 10
aaaugauttu auutagttg                                                  19

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 11
ctacccacca accatc                                                        16

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccaccaacca tcatatc                                                       17

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (17)..(17)
<223> OTHER INFORMATION: BHQ1-dT

<400> SEQUENCE: 13
ttgatcgcgg ggttcgt                                                       17

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (16)..(16)
<223> OTHER INFORMATION: BHQ1-dT

<400> SEQUENCE: 14
cgcgttgatc gcgggt                                                        16

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (17)..(17)
<223> OTHER INFORMATION: BHQ1-dT

<400> SEQUENCE: 15
aaccccgcga tcaacgt                                                       17

<210> SEQ ID NO 16
<211> LENGTH: 16
<212> TYPE: DNA
```

```
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' FAM
<220> FEATURE:
<221> NAME/KEY: modified_base
<222> LOCATION: (16)..(16)
<223> OTHER INFORMATION: BHQ1-dT

<400> SEQUENCE: 16
ccgcgatcaa cgcgct                                                    16

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' 3SpC3

<400> SEQUENCE: 17
catatcaaac cccacaatca acaca                                          25

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' 3SpC3

<400> SEQUENCE: 18
tttagttgtg tgttgattgt ggggtt                                         26

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gttgtgtgtt gattgtg                                                   17

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
catcatatca aacccca                                                   17

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: 5' MGB

<400> SEQUENCE: 21
aaaccccaca atcaacacac aactaaa                                          27

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' MGB

<400> SEQUENCE: 22
aaaccccaca atcaacacac aac                                              23

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' MGB

<400> SEQUENCE: 23
aaaccccaca atcaacacac aa                                               22

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' MGB

<400> SEQUENCE: 24
tgtgttgatt gtggggtttg atatga                                           26

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' MGB

<400> SEQUENCE: 25
tgtgttgatt gtggggtttg atatg                                            25

<210> SEQ ID NO 26

<400> SEQUENCE: 26

000

<210> SEQ ID NO 27
<211> LENGTH: 24
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<223> OTHER INFORMATION: 5' MGB

<400> SEQUENCE: 27
tgtgttgatt gtggggtttg atat                                          24

<210> SEQ ID NO 28
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Methylated cytosine
<220> FEATURE:
<221> NAME/KEY: modified_base
<222> LOCATION: (27)..(27)
<223> OTHER INFORMATION: Methylated cytosine
<220> FEATURE:
<221> NAME/KEY: modified_base
<222> LOCATION: (34)..(34)
<223> OTHER INFORMATION: Methylated cytosine
<220> FEATURE:
<221> NAME/KEY: modified_base
<222> LOCATION: (36)..(36)
<223> OTHER INFORMATION: Methylated cytosine
<220> FEATURE:
<221> NAME/KEY: modified_base
<222> LOCATION: (43)..(43)
<223> OTHER INFORMATION: Methylated cytosine
<220> FEATURE:
<221> NAME/KEY: modified_base
<222> LOCATION: (45)..(45)
<223> OTHER INFORMATION: Methylated cytosine

<400> SEQUENCE: 28
gacccgctgc ccaccagcca tcatgtcgga ccccgcggtc aacgcgcagc tggatgggat  60
cattt                                                              65

<210> SEQ ID NO 29
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Methylated cytosine
<220> FEATURE:
<221> NAME/KEY: modified_base
<222> LOCATION: (22)..(22)
<223> OTHER INFORMATION: Methylated cytosine
<220> FEATURE:
<221> NAME/KEY: modified_base
<222> LOCATION: (29)..(29)
<223> OTHER INFORMATION: Methylated cytosine
<220> FEATURE:
<221> NAME/KEY: modified_base
<222> LOCATION: (31)..(31)
<223> OTHER INFORMATION: Methylated cytosine
<220> FEATURE:
<221> NAME/KEY: modified_base
<222> LOCATION: (38)..(38)
<223> OTHER INFORMATION: Methylated cytosine
<220> FEATURE:
<221> NAME/KEY: modified_base
```

```
<222> LOCATION: (60)..(60)
<223> OTHER INFORMATION: Methylated cytosine

<400> SEQUENCE: 29
aaatgatccc atccagctgc gcgttgaccg cggggtccga catgatggct ggtgggcagc    60
gggtc                                                                65

<210> SEQ ID NO 30
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: Methylated cytosine
<220> FEATURE:
<221> NAME/KEY: modified_base
<222> LOCATION: (27)..(27)
<223> OTHER INFORMATION: Methylated cytosine
<220> FEATURE:
<221> NAME/KEY: modified_base
<222> LOCATION: (34)..(34)
<223> OTHER INFORMATION: Methylated cytosine
<220> FEATURE:
<221> NAME/KEY: modified_base
<222> LOCATION: (36)..(36)
<223> OTHER INFORMATION: Methylated cytosine
<220> FEATURE:
<221> NAME/KEY: modified_base
<222> LOCATION: (43)..(43)
<223> OTHER INFORMATION: Methylated cytosine
<220> FEATURE:
<221> NAME/KEY: modified_base
<222> LOCATION: (45)..(45)
<223> OTHER INFORMATION: Methylated cytosine

<400> SEQUENCE: 30
gattcgttgt ttattagtta ttatgtcgga tttcgcggtt aacgcgtagt tggatgggat    60
tattt                                                                65

<210> SEQ ID NO 31
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Methylated cytosine
<220> FEATURE:
<221> NAME/KEY: modified_base
<222> LOCATION: (22)..(22)
<223> OTHER INFORMATION: Methylated cytosine
<220> FEATURE:
<221> NAME/KEY: modified_base
<222> LOCATION: (29)..(29)
<223> OTHER INFORMATION: Methylated cytosine
<220> FEATURE:
<221> NAME/KEY: modified_base
<222> LOCATION: (31)..(31)
<223> OTHER INFORMATION: Methylated cytosine
<220> FEATURE:
<221> NAME/KEY: modified_base
<222> LOCATION: (38)..(38)
<223> OTHER INFORMATION: Methylated cytosine
<220> FEATURE:
<221> NAME/KEY: modified_base
<222> LOCATION: (60)..(60)
```

```
<223> OTHER INFORMATION: Methylated cytosine

<400> SEQUENCE: 31
aaatgatttt atttagttgc gcgttgatcg cggggttcga tatgatggtt ggtgggtagc    60
gggtt                                                                65

<210> SEQ ID NO 32
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gatttgttgt ttattagtta ttatgttgga ttttgtggtt aatgtgtagt tggatgggat    60
tattt                                                                65

<210> SEQ ID NO 33
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aaatgatttt atttagttgt gtgttgattg tggggtttga tatgatggtt ggtgggtagt    60
gggtt                                                                65
```

DETECTION OF BISULFITE CONVERTED NUCLEOTIDE SEQUENCES

SEQUENCE LISTING

The instant application contains a Sequence Listing which has been submitted electronically in ASCII format and is hereby incorporated by reference in its entirety. Said ASCII copy, created on May 13, 2014, is named 01886-2006US02_SL.txt and is 11,093 bytes in size.

BACKGROUND

Bisulfite sequencing is a method that uses bisulfite to determine the methylation pattern of DNA. DNA methylation is a biochemical process involving the addition of a methyl group to the cytosine or adenine DNA nucleotides. DNA methylation stably alters the expression of genes in cells as cells divide and differentiate from embryonic stem cells into specific tissues. In bisulfite sequencing (also known as bisulfite conversion) target nucleic acids are first treated with bisulfite reagents that specifically convert un-methylated cytosines to uracils while having no impact of methylated cytosine. One unwanted consequence of bisulfite conversion is that the double-stranded conformation of the original target is disrupted due to loss of sequence complementarity. The target sequences exist as two separate single-stranded DNAs during sample preparation and analytical or diagnostic testing. Target nucleic acid sequences frequently also exist at very low concentrations. This is an especially important consideration for circulating tumor DNA such as the case for SEPTIN 9 (mS9). Therefore, what is needed are reagents and methods for the enhanced detection of target nucleic acid sequences after bisulfite conversion.

SUMMARY OF THE INVENTION

The present invention is directed towards reagents and methods for the enhanced detection of target nucleic acids after bisulfite conversion (also known as bisulfite sequencing or bisulfite treatment). The present invention addresses this need by providing reagents and methods for the enhanced detection of target nucleic acids. The present invention also teaches strategies for the general application of the methods taught herein.

The assay design strategy of the invention is to ensure that both of the nucleic acid strands formed as a result of the chemical conversion cause by the bisulfite treatment serve as targets for analytical testing. Examples of suitable analytical testing are target amplification and/or signal amplification. Detection of the nucleic acids of very low concentration is improved by targeting both strands after the conversion of the un-methylated cytosines to uracils as opposed to the commonly used single strand detection of the prior art.

In an embodiment of the present invention, primers specific for the methylated SEPTIN 9 gene (mS9) are provided. In this regard, the present invention is also directed to a set of primers for amplification of mS9 in a sample of nucleic acid from a human is also provided. The set of primers comprises at least one primer selected from the group consisting of:

(a) an oligonucleotide comprising the nucleotide sequence AAAuGAuTTuAuuTAGTTG [SEQ ID NO: 10] at its 3' terminus, (b) an oligonucleotide comprising the nucleotide sequence CTACCCACCAACCATC [SEQ ID NO: 11] at its 3' terminus, (c) an oligonucleotide comprising the nucleotide sequence CCACCAACCATCATATC [SEQ ID NO: 12] at its 3' terminus.

The present invention contemplates a method of detecting nucleotide sequences comprising at least one unmethylated cytosine residue treated with bisulfite reagents comprising: providing, i) a sample suspected of comprising the target nucleic acid, ii) one or more primers specific for the bisulfite converted sense strand of nucleic acid, iii) one or more primers specific for the bisulfite converted antisense strand of the nucleic acid; amplifying both the sense and antisense strands of any target nucleic acid present in the sample; and detecting any amplified nucleic acid.

The present invention is not limited to any specific sample or sample type. For example, sample materials may include bodily fluids including plasma, serum, blood, spinal fluid, semen, vaginal fluids, sputum and saliva, cerebrospinal fluid, lymphatic fluid and digestive fluids. Other sample materials may include isolated or enriched cell populations and tissues. Samples may be fresh or fixed (preserved). Fixed samples may be embedded (for example, paraffin embedded). Further, samples may be obtained from archeological digs, i.e., prehistoric tissues such as bones may yield nucleic acids that can be enriched or isolated by the methods of the present invention. Certain sample types may require pretreatment to, for example, concentrate the sample (by, for example, centrifugation of suspended cells) or break apart large sample sources (for example, grinding of bones or digestive breakdown of tissues). Such pretreatments are primary to obtain starting materials that are more easily workable by the methods of the present invention. With regard to tissues, nucleic acid may be derived from tissue, sputum, stool, urine, or cerebrospinal fluid.

It is further contemplated that the sample is suspected of comprising mS9. Further, it is contemplated that the sample is obtained from a subject being screened for colorectal cancer and/or from a subject suspected of having colorectal cancer and/or from a subject being treated for colorectal cancer. It is further contemplated that the amplification nucleic acid in said sample is compared to one or more samples taken previously from the same subject.

DETAILED DESCRIPTION OF THE INVENTION

Definitions

Figure 1:
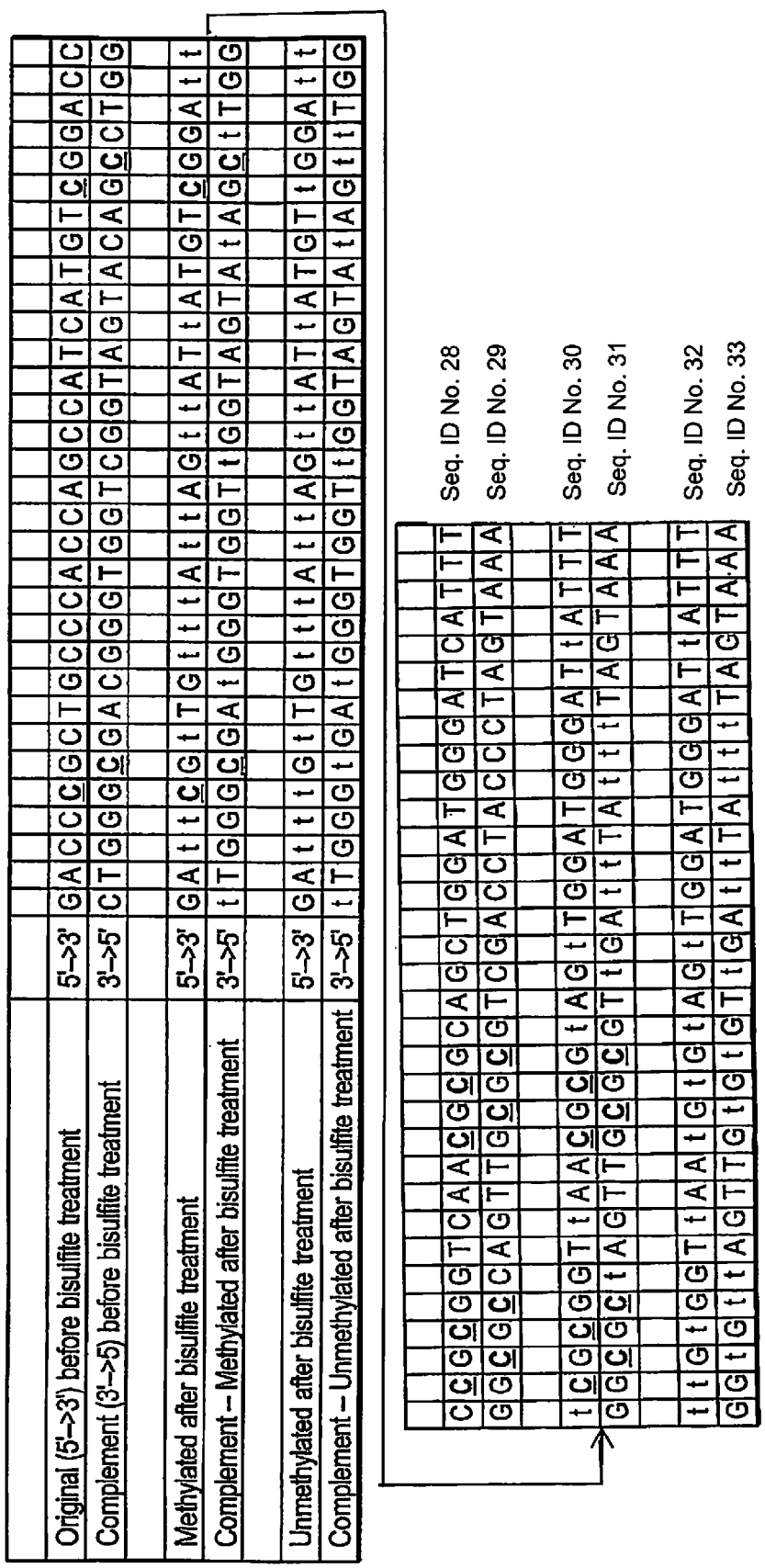
FIG. 1 shows sequences for original and complementary sequences before and after bisulfite treatment (SEQ ID NOS 28-33, respectively, in order of appearance). The treatment disrupts the complementarity of the two strands after treatment. "C" is methylated cytosine.

The following definitions are relevant to the present disclosure:

The term "about" refers to approximately a +/−10% variation from the stated value. It is to be understood that such a variation is always included in any given value provided herein, whether or not specific reference is made to it.

The term "bisulfite reagent" refers to a reagent comprising bisulfite, disulfite, hydrogen sulfite or combinations thereof, useful as disclosed herein to distinguish between methylated and unmethylated CpG dinucleotide sequences.

The term "allele-specific primer" in the context of the present disclosure refers to a primer (see "primer") that hybridizes to a target sequence such that the 3' end, usually the 3' nucleotide, of the primer aligns with a site of interest, e.g., a sequence of mS9, and is exactly complementary to either the wild-type allele or a mutant allele at the codon of the target nucleic acid of interest. The use of an allele-specific primer enables discrimination between alleles based on differential formation of extension products during nucleic acid, e.g., DNA, amplification.

The term "detectable oligonucleotide" refers to an oligonucleotide that selectively hybridizes to a target nucleic acid under suitable conditions and can be detected.

The term "high-affinity nucleic acid analogue" refers to a modified nucleic acid that hybridizes to a complementary nucleic acid, such as a deoxyribonucleic acid (DNA), with higher affinity than an unmodified nucleic acid having the same base sequence. High-affinity nucleic acids include, but are not limited to, locked nucleic acids (LNAs), peptide nucleic acids (PNAs), hexitol nucleic acids (HNAs), phosphoramidates, and the like.

The term "hybridization" refers to the formation of a duplex structure by complementary base pairing between two single-stranded nucleic acids. Hybridization can occur between exactly complementary nucleic acid strands or between complementary nucleic acid strands that contain a low number of mismatches.

The terms "nucleic acid," "polynucleotide," and "oligonucleotide" refer to primers, detectable oligonucleotides, and oligomers, irrespective of length, and include polydeoxyribonucleotides, polyribonucleotides, and any other N-glycoside of a modified/unmodified, purine/pyrmidine base. Examples include single-stranded DNA (ssDNA), double-stranded DNA (dsDNA), single-stranded RNA (ssRNA), and double-stranded RNA (dsRNA). Such molecules can comprise phosphodiester linkages or modified linkages including, but not limited to, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations thereof. Such molecules can comprise adenine, guanine, thymine, cytosine and/or uracil, as well as other modified, non-standard, or derivatized bases. Alternatively or additionally, such molecules can comprise one or more modified sugar moieties.

The term "peptide nucleic acid (PNA)" refers to a synthetic DNA analog in which the normal phosphodiester backbone is replaced with an N-(2-aminoethyl)glycine chain. Its nucleobases complement DNA or RNA in the same A-T(U) and G-C manner (Nielsen, et al., Science 254: 1497-1500 (1991); Hanvey, et al., Science 258: 1481-1485 (1992); and Egholm, et al., Nature 365: 566-568 (1993)). The artificial backbone renders PNA resistant to nucleases. PNA can be synthesized in accordance with methods known in the art (see, e.g., Hyrup, et al., Bioorg. Med. Chem. 4: 5-23 (1996); Int'l Pat. App. Pub. Nos. WO 92/20702 and 92/20703; and U.S. Pat. No. 5,539,082, the contents of all of which are incorporated herein by reference for their teachings regarding same). Two important features make PNA a superior PCR clamp for specific alleles. It cannot serve as a primer for polymerization. It cannot serve as a substrate for exonuclease activity by Taq polymerase. In addition, the melting temperature of a perfectly matched PNA-DNA duplex is higher than that of a DNA-DNA duplex of the same length; thus, the PNA-DNA duplex is more stable. A single mismatch in a PNA-DNA hybrid will cause a drop in the melting temperature of about 10-18° C. (Kyger, et al., Anal. Biochem. 260: 142-148 (1998)). Therefore, over an appropriate temperature range PNA can specifically block primer/detectable oligonucleotide annealing or chain elongation on a perfectly matched template without interfering with reactions on templates with mismatched base(s) (Sun, et al., Nat. Biotechnol. 20: 186-189 (2002); Thiede, et al., Nucleic Acids Res. 24: 983-984 (1996); and Taback, et al., Int. J. Cancer 111: 409-414 (2004)), which is referred to as PNA-mediated PCR clamping (Orum, et al., Nucleic Acids Res. 21: 5332-5336 (1993)). The large difference in melting temperature between perfectly matched and mismatched hybrids makes PNA a good sensor of point mutations (see, e.g., Karadag, et al., Nucleic Acids Res. 32: e63 (2004); Taback, et al. (2004), supra; Hancock, et al., Clin. Chem. 48: 2155-2163 (2002); Takiya, et al., Biosci. Biotechnol. Biochem. 68: 360-368 (2004); Kirishima, et al., J. Hepatol. 37: 259-265 (2002); and Ohishi, et al., J. Med. Virol. 72: 558-565 (2004)). U.S. Pat. App. Pub. No. 2004/0014105 discloses methods for the selective enrichment of polynucleotides that are present in a sample in low abundance. The method uses enzymatically non-extendable nucleobase oligomer (e.g., PNA) as a PCR clamp to block selectively polymerase activity on polynucleotides that are present in the sample in high abundance, thereby resulting in an enrichment of less abundant species in the sample. "PNA" may include a PNA clamp. Clamping operates by physical competition between a PNA and a DNA primer or probe for a common target site, thereby interfering with primer elongation.

The term "polymerase chain reaction (PCR)" is a method of making copies of a DNA sequence. The method employs thermal cycling (i.e., cycles of heating and cooling for denaturation (or melting) and replication of the DNA, respectively). Primers, which are short DNA fragments containing sequences complementary to the DNA sequence to be copied, and a heat-stable DNA polymerase, such as the one from Thermus aquaticus, which is referred to as Taq polymerase, are used to select the DNA sequence and copy it (see, e.g., U.S. Pat. Nos. 4,683,195; 4,800,195, and 4,965,188, all of which are incorporated by reference herein for their teachings regarding same). With repeated cycling the copies, which are made, are used as templates for generating further copies (i.e., a chain reaction). PCR techniques include, but are not limited to, standard PCR, allele-specific PCR, assembly PCR, asymmetric PCR, digital PCR, Hot-start PCR, intersequence-specific PCR, inverse PCR, ligation-mediated PCR, methylation-specific PCR, mini-primer PCR, nested PCR, overlap-extension PCR, real-time PCR, reverse transcription-PCR, solid phase PCR, thermal asymmetric interlaced PCR, and Touchdown PCR.

The term "primer" as used herein refers to an oligonucleotide that initiates template-dependent nucleic acid synthesis. In the presence of a nucleic acid template, nucleoside triphosphate precursors, a polymerase, and cofactors, under suitable conditions of temperature and pH, the primer can be extended at its 3' terminus by the addition of nucleotides by the polymerase to yield a primer extension product. The primer may vary in length depending on the particular conditions employed and the purpose of the amplification. For example, a primer for amplification for a diagnostic purpose is typically from about 15 to about 35 nucleotides in length. The primer must be of sufficient complementarity to the desired template to prime the synthesis of the desired extension product. In other words, the primer must be able to anneal with the desired template strand in a manner sufficient to provide the 3' hydroxyl moiety of the primer in appropriate juxtaposition for use in the initiation of synthesis by a polymerase. It is not necessary for the primer to be an exact complement of the desired template. For example, a non-complementary nucleotide sequence can be present at the 5' end of an otherwise complementary primer. Alternatively, non-complementary bases can be interspersed within the oligonucleotide primer, provided that the primer sequence has sufficient complementarity with the sequence of the desired template strand to provide a template-primer complex for the synthesis of the extension product.

The term "specifically hybridize(s)," as used herein, refers to the ability of a given nucleic acid, such as a primer or detectable oligonucleotide, to bind specifically to another nucleic acid.

The terms "stringent" or "sequence-specific" hybridization conditions refers to conditions under which exactly complementary nucleic acid strand will preferentially hybridize. Stringent hybridization conditions are well-known in the art. Stringent conditions are sequence-dependent and will be different under different circumstances. Generally, stringent conditions are selected to be about 5° C. lower than the thermal melting point ($T_m$) for the specific sequence under defined conditions of pH and ionic strength at which 50% of the base pairs are dissociated.

The term "substantially complementary" refers to sequences that are complementary except for minor regions of mismatches. Typically, the total number of mismatches in a nucleic acid that is about 15 nucleotides in length is about 3 nucleotides or less.

The terms "target sequence" and "target region" refer to a region of a nucleic acid that it to be detected, or detected and analyzed, and comprises the polymorphic site of interest, i.e., mS9 as one example in the context of the present disclosure.

The terms "colorectal cancer" and "colon cancer" are used interchangeably herein to refer to any cancerous neoplasia of the colon (including the rectum) as recognized by the American Cancer Association, American Medical Association or other medical organization know to one of ordinary skill in the art The term "methylation state" or "methylation status" refers to the presence or absence of 5-methylcytosine ("5-mCyt") at one or a plurality of CpG dinucleotides within a DNA sequence. Methylation states at one or more particular CpG methylation sites (each having two CpG dinucleotide sequences) within a DNA sequence include "unmethylated," "fully-methylated" and "hemi-methylated."

The term "hemi-methylation" or "hemimethylation" refers to the methylation state of a double stranded DNA wherein only one strand thereof is methylated.

The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

DNA Methylation

DNA methylation was first the discovered epigenetic mark. Epigenetics is the study of changes in gene expression or cellular phenotype caused by mechanisms other than changes in the underlying DNA sequence. Methylation predominately involves the addition of a methyl group to the carbon-5 position of cytosine residues of the dinucleotide CpG and is associated with repression or inhibition of transcriptional activity.

DNA methylation may affect the transcription of genes in two ways. First, the methylation of DNA itself may physically impede the binding of transcriptional proteins to the gene and, second and likely more important, methylated DNA may be bound by proteins known as methyl-CpG-binding domain proteins (MBDs). MBD proteins then recruit additional proteins to the locus, such as histone deacetylases and other chromatin remodeling proteins that can modify histones, thereby forming compact, inactive chromatin, termed heterochromatin. This link between DNA methylation and chromatin structure is very important. In particular, loss of methyl-CpG-binding protein 2 (MeCP2) has been implicated in Rett syndrome; and methyl-CpG-binding domain protein 2 (MBD2) mediates the transcriptional silencing of hypermethylated genes in cancer.

DNA methylation is an important regulator of gene transcription and a large body of evidence has demonstrated that genes with high levels of 5-methylcytosine in their promoter region are transcriptionally silent, and that DNA methylation gradually accumulates upon long-term gene silencing. DNA methylation is essential during embryonic development and in somatic cells patterns of DNA methylation are generally transmitted to daughter cells with a high fidelity. Aberrant DNA methylation patterns—hypermethylation and hypomethylation compared to normal tissue—have been associated with a large number of human malignancies. See, Veersteeg, R. 1997. Aberrant methylation in cancer. *American Journal of Human Genetics*. 60:751-754. Hypermethylation typically occurs at CpG islands in the promoter region and is associated with gene inactivation. Global hypomethylation has also been implicated in the development and progression of cancer through different mechanisms.

The detection of methylated DNA, therefore, can be useful in the diagnosis of certain cancers and, potentially, for following treatment efficacy.

One example of a cancer wherein bisulfite sequencing has proven useful is for the screening of colorectal cancer wherein the detection of methylated Septin 9 (mS9) is used as a biomarker. Other examples of target sequences for bisulfite conversion are esophageal squamous cell carcinoma (Baba, et al., Surg. Today, 2013, January 5 ePub), breast cancer (Dagdemir, et al., In vivo, 2013, 27(1):1-9), prostate cancer (Willard and Koochekpour, Am. J. Cancer Res. 2012, 2(6): 620-657, ePub Nov. 20, 2012), non-Hodgkin's lymphomas (Yin, et al., Front Genet, 2012, 3:233, ePub Nov. 8, 2012), oral cancers (Gasche and Goel, Future Onocol, 2012,8(11):1407-1425), etc. One of ordinary skill in the art will appreciate that the methods of the present invention are applicable to and easily adapted to the improved detection of these and other cancers known to be manifested at least in part by hypermethylation or hypomethylation of target gene sequences. Likewise, other medical conditions known to those of skill line art that wherein hypermethylation and/or hypomethylation are part of the known etiology will have improved detection with the application of the methods of the present invention.

Septin 9

Septins are a group of highly-conserved GTP binding proteins found in eukaryotes. Although the present invention is not limited by theory, the latest research in human cells suggests that septins build 'cages' around bacterial pathogens, immobilizing the harmful microbes and preventing them from invading other healthy cells. Septin-9 is a protein that in humans is encoded by the SEPT9 gene. The v2 region of the SEPT9 promoter has been shown to be methylated in colorectal cancer tissue compared with normal colonic mucosa. www.transatlantic-symposium.de/content/_docs/doc1241003872263.pdf. Using highly sensitive real time PCR assays, methylated SEPT9 was detected in the blood of colorectal cancer patients. This alternate methylation pattern in cancer samples is suggestive of an aberrant activation or repression of the gene compared to normal tissue samples. Grutzmann, Robert, et al., (November 2008). Najbauer, Joseph. ed. "Sensitive Detection of Colorectal Cancer in Peripheral Blood by Septin 9 DNA Methylation Assay". *PLoS ONE* 3 (11): 1-8; deVos T, et al., (2009). "Circulating methylated SEPT9 DNA in plasma is a biomarker for colorectal cancer". *Clin Chem.* 55 (7): 1337-1346. Commercial PCR-based tests are now available for screening patients for SEPT9 hypermethylation (ARUP Laboratories, Salt Lake City, Utah). However, these tests are subject to the limitations as described above with regard to sensitivity and specificity.

Colorectal Cancer

A colon neoplasia or colorectal cancer is any cancerous or precancerous growth located in, or derived from, the colon. The colon is a portion of the intestinal tract that is roughly three feet in length, stretching from the end of the small intestine to the rectum. Viewed in cross section, the colon consists of four distinguishable layers arranged in concentric rings surrounding an interior space, termed the lumen, through which digested materials pass. In order, moving outward from the lumen, the layers are termed the mucosa, the submucosa, the muscularis propria and the subserosa. The mucosa includes the epithelial layer (cells adjacent to the lumen), the basement membrane, the lamina propria and the muscularis mucosae. In general, the "wall" of the colon is intended to refer to the submucosa and the layers outside of the submucosa. The "lining" is the mucosa.

Precancerous colon neoplasias are referred to as adenomas or adenomatous polyps. Adenomas are typically small mushroom-like or wart-like growths on the lining of the colon and do not invade into the wall of the colon. Adenomas may be visualized through a device such as a colonoscope or flexible sigmoidoscope. Several studies have shown that patients who undergo screening for and removal of adenomas have a decreased rate of mortality from colon cancer. For this and other reasons, it is generally accepted that adenomas are an obligate precursor for the vast majority of colon cancers. When a colon neoplasia invades into the basement membrane of the colon, it is considered a colon cancer, as the term "colon cancer" is used herein. As with all cancers, colon cancer is graded in a numerical system from 1-4 with the higher numbers indicating more advanced stages of the disease.

Bisulfite Conversion

Herein, the terms "bisulfite conversion," "bisulfite sequencing" and "bisulfite treatment" are synonymous unless otherwise indicated.

Bisulfite conversion is the use of bisulfite reagents to treat DNA to determine its pattern of methylation. The treatment of DNA with bisulfite converts cytosine residues to uracil but leaves 5-methylcytosine residues unaffected. Thus, bisulfite treatment introduces specific changes in the DNA sequence that depend on the methylation status of the individual cytosine residues. Various analyses can be performed on the altered sequence to retrieve this information. The objective of this analysis is therefore to differentiate between single nucleotide polymorphisms (SNP) resulting from the bisulfite conversion. U.S. Pat. No. 7,620,386 and US Patent Application Publication 2006/0134643, both of which are incorporated herein by reference, exemplify methods known to one of ordinary skill in the art with regard to detecting sequences altered due to bisulfite conversion. Further, work published by Grunau, et al., provides additional exemplification of methods known to one of ordinary skill in the art with regard to methods of bisulfite conversion and detection of altered residues as a result of the conversion. Additionally, Paul C. L. and Clark, S. J. (1996) Cytosine methylation: quantitation by automated genomic sequencing and GENESCAN™ analysis. Biotechniques, 21, 126-133; Gonzalgo M. L. and Jones, P. A. (1997) Rapid quantitation of methylation differences at specific sites using methylation-sensitive single nucleotide primer extension (Ms-SNuPE). Nucleic Acids Res., 25, 2529-2531; Herman J. G., et al. (1996) Methylation-specific PCR: a novel PCR assay for methylation status of CpG islands. Proc. Natl Acad. Sci. USA, 93, 9821-9826, all provide further exemplification of what one of ordinary skill in the art had knowledge of with regard to bisulfite conversion and detection of altered residues as a result of the conversion, at the time of the invention.

Several methods are known to one of ordinary skill in the art as is exemplified in the following review articles. Fraga M F, Esteller M (September 2002). "DNA methylation: a profile of methods and applications". *Bio Techniques* 33 (3): 632, 634, 636-49; El-Maarri O (2003). "Methods: DNA methylation". *Adv. Exp. Med. Biol.* Advances in Experimental Medicine and Biology 544: 197-204; Laird P W (April 2003). "The power and the promise of DNA methylation markers". *Nat. Rev. Cancer* 3 (4): 253-66; Frommer M, McDonald L E, Millar D S, et al. (March 1992). "A genomic sequencing protocol that yields a positive display of 5-methylcytosine residues in individual DNA strands". *Proc. Natl. Acad. Sci. U.S.A.* 89 (5): 1827-31; Fürst, R W, et al., A Differentially Methylated Single Cpg-Site Is Correlated With Estrogen Receptor Alpha Transcription. J Steroid Biochem Mol Biol. 2012 May, 130(1-2):96-104, Epub 2012 February 10.

An exemplary method for the detection of bisulfite treatment of nucleic acid include the use of primer pairs (forward and reverse) primer pairs are designed themselves to be "methylated-specific" by including sequences complementing only unconverted 5-methylcytosines, or, on the converse, "unmethylated-specific," complementing thymines converted from unmethylated cytosines. Methylation is determined by the ability of the specific primer to achieve amplification.

Further methodology using amplified DNA analyzes the products using melting curve analysis. This method amplifies bisulfite-converted DNA with both methylated-specific and unmethylated-specific primers, and determines the quantitative ratio of the two products by comparing the differential peaks generated in a melting curve analysis. A high-resolution melting analysis methods are known to one of ordinary skill in the art that uses both real-time quantification and melting analysis, in particular, for sensitive detection of low-level methylation The bisulfite reaction may be performed according to standard techniques. For example and briefly, approximately 1 microgram of genomic DNA (amount of DNA can be less when using micro-dissected DNA specimens) is denatured for 15 minutes at 45° C. with 2N NaOH followed by incubation with 0.1M hydroquinone and 3.6M sodium bisulfite (pH 5.0) at 55° C. for 12 hours (appropriate range is 4-12 hours). The DNA is then purified from the reaction mixture using standard (commercially-available) DNA miniprep columns, or other standard techniques for DNA purification are also appropriate. The purified DNA sample is resuspended in 55 microliters of water and 5 microliters of 3N NaOH is added for a desulfonation reaction, preferably performed at 40° C. for 5-10 minutes. The DNA sample is then ethanol-precipitated and washed before being resuspended in an appropriate volume of water and amplified.

Bisulfite converts un-menthylated cytosine to uracil while having no impact on methylated cytosine. This information is useful in connection with expression studies, but the conversion has an adverse affect on downstream analytical and diagnostic testing. For example, bisulfite conversion destroys complementarity between two strands of nucleic acid. This result in the prevention of the amplification of the now non-complementary strand of nucleic acid when the prior art method of providing primers for the first strand (e.g., the sense strand) because the target sequences exist as two separate single-stranded DNAs during sample preparation and analytical or diagnostic testing. Also, target nucleic acid sequences frequently also exist at very low concentrations exasperating this problem.

Figure 2:
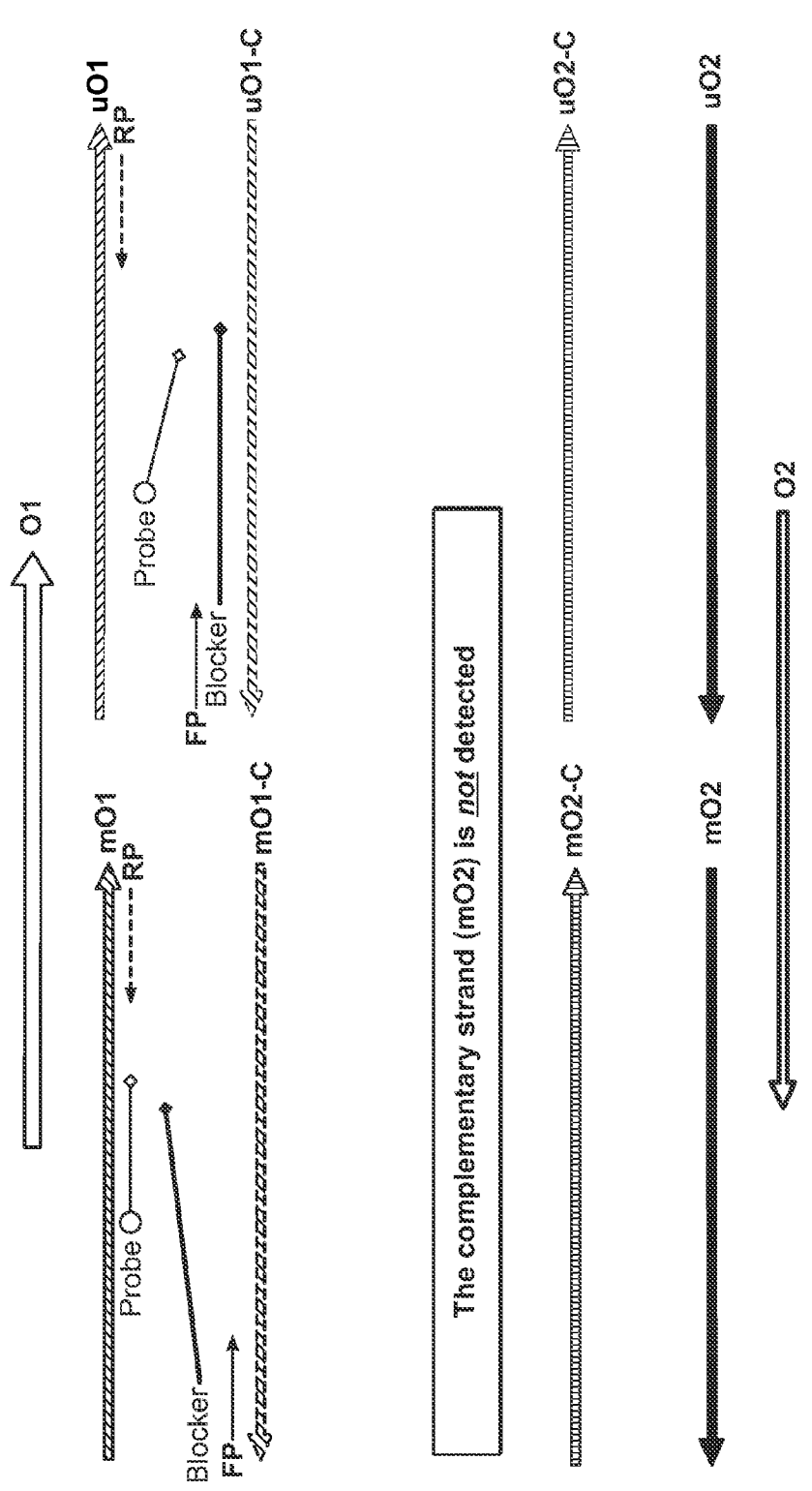
FIG. 2 shows the prior art method wherein only one strand (mO1) is targeted.
Figure 3:
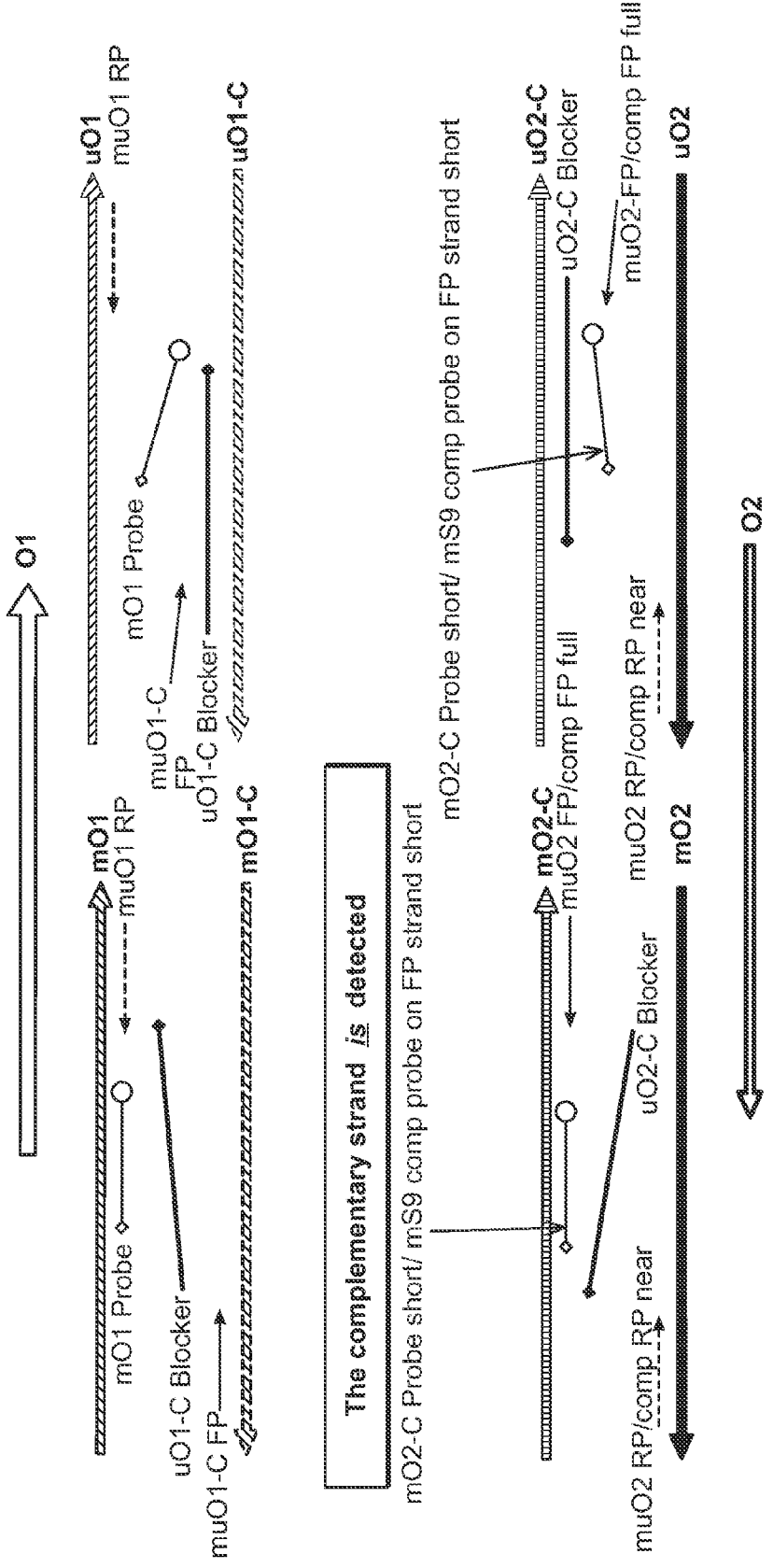
FIG. 3 shows the advancement of the present invention wherein both strands (mO1 and mO2) are targeted.

The present invention is directed towards reagents and methods for the enhanced detection of target nucleic acids after bisulfite conversion by providing reagents and methods for the enhanced detection of target nucleic acids. The assay design strategy of the invention is to ensure that both of the nucleic acid strands formed as a result of the chemical conversion cause by the bisulfite treatment serve as targets for analytical testing (see, FIG. 3). In this regard, primers are provided for both strands of the target nucleic acid ensuring the amplification of both strands and effectively doubling the amplified nucleic acid generated and/or signal generated. Furthermore, the present invention ensures that detection of the nucleic acids of very low concentration is improved by targeting both strands after the conversion of the un-methylated cytosines to uracils. The present reagents and methods provide for greatly enhanced target detection as opposed to the commonly used single strand detection methods of the prior art (see, FIG. 2). FIGS. 2 and 3 schematically demonstrate the advantage of the present invention over the prior art methods. By providing for example, primers muO2 FP/comp FP full and mu02 RP/comp RP near in addition to muO1 RP and mu01-C FP, both strands of the bisulfite converted target nucleic acids are amplified. The blocker sequences in FIGS. 2 and 3 ensure that no significant amplification of the un-methylated strands (uO1 and uO2-C) takes place.

Samples from which nucleic acids are isolated may come from any suitable biological source. For example, samples may be derived from body fluid (including blood, serum and plasma) and from tissue, sputum, stool, urine, and cerebrospinal fluid. Further, the samples may be preserved specimens.

PCR

Target sequences are amplified with techniques known in the art. The technique of choice is polymerase chain reaction (PCR). PCR amplification can be performed by standard PCR techniques, following a manufacturer's instructions. The Abbott m2000 system is a device that automates PCR reactions based on input from the user (Abbott, Abbott Park, Ill.)

The amplification reaction can, and preferably does, comprise an internal control (IC) nucleic acid and a pair of primers for amplifying the IC nucleic acid. When the amplification reaction comprises an IC nucleic acid, the conditions that promote amplification also promote amplification of the IC nucleic acid. Any suitable sequence can be used as the IC. Examples of IC target sequences include those used in the Exemplification section, below.

Any suitable sample of a tissue or a body fluid can be used as the source of the sample of nucleic acid, i.e., DNA or RNA. Typically, the source is a tumor or cells/tissues from a metastatic site or blood (or component thereof). Blood, plasma, serum, lymph, and tumor biopsies, for example, can be used. Other samples include urine, cerebrospinal fluid, pleural fluid, sputum, peritoneal fluid, bladder washings, secretions (e.g., breast), oral washings, touch preparations, and fine-needle aspirates. A plasma or whole blood can be preserved, such as by the addition of a chelating agent, e.g., ethylenediaminetetraacetic acid (EDTA) or a salt thereof, such as a disodium salt or a calcium disodium salt. A proteinase, such as proteinase K, can be added to the sample to digest unwanted proteins.

Tissue samples can be generally preserved as formalin-fixed, paraffin-embedded (FFPE) blocks. Tissue sections of varying thickness, such as 5 µm, are cut from such tissue blocks and either left unmounted or mounted onto a solid support, such as a slide, by standard means. The cellular morphology of the tissue sample is revealed using a variety of fixatives and/or stains and visualized microscopically. If the density of cells, such as cancer cells, e.g., melanoma cells, in a tissue sample is sufficient (greater than about 1%), the section is scraped from the slide, and DNA can be extracted directly from the total tissue sample without further purification. Alternatively, if the density of cells, such as cancer cells, e.g., melanoma cells, in a tissue sample is low (less than about 1%), additional procedures to enrich the tissue sample for melanoma cells can be performed. DNA also can be isolated from fresh/frozen tissue, a fine-needle aspirate, or peripheral blood.

The sample may be prepared for assay using any suitable method as is known in the art. Desirably, the method extracts and concentrates nucleic acids. The method also desirably makes the target sequence accessible for amplification, and removes potential inhibitors of amplification from the extract.

DNA can be isolated from peripheral blood using, for example, a DNeasy DNA isolation kit, a QIAamp DNA blood kit, or a PAXgene blood DNA kit from Qiagen Inc. (Valencia, Calif.), or other methods known to one of ordinary skill in the art. DNA from other tissue samples also can be obtained using a DNeasy DNA isolation kit. Any other DNA extraction and purification technique also can be used, including liquid-liquid and solid-phase techniques ranging from phenol-chloroform extraction to automated magnetic bead nucleic acid capture systems. RNA can be isolated and reverse-transcribed and the resulting cDNA can be amplified (e.g., reverse-transcription polymerase chain reaction (RT-PCR) as described in U.S. Pat. Nos. 5,310,652; 5,322,770; 5,561,058; 5,641,864; and 5,693,517, for example).

Once nucleic acid has been obtained, it can be contacted with primers that result in specific amplification of a mutant sequence, if the mutant sequence is present in the sample. "Specific amplification" means that the primers amplify a specific mutant sequence and not other mutant sequences or the wild-type sequence. See, e.g., PCR Technology: Principles and Applications for DNA Amplification (Erlich, Editor, Freeman Press, NY (1992)); PCR Protocols: A Guide to Methods and Applications (Innis, et al., Editors, Academic Press, San Diego, Calif. (1990)); Current Protocols in Molecular Biology (Ausubel, 1994-1999, including supplemental updates through April 2004); and Molecular Cloning: A Laboratory Manual (Sambrook & Russell, 3rd ed., 2001). Allele-specific amplification-based methods or extension-based methods are described in Int'l Pat. App. Pub. No. WO 93/22456 and U.S. Pat. Nos. 4,851,331; 5,137,806; 5,595,890; and 5,639,611, all of which are specifically incorporated herein by reference for their teachings regarding same. While methods such as ligase chain reaction, strand displacement assay, and various transcription-based amplification methods can be used (see, e.g., review by Abramson and Myers, Current Opinion in Biotechnology 4:41-47 (1993)), PCR, in particular PCR employing clamps, such as PNA clamps, is preferred.

Multiple allele-specific primers, such as multiple mutant alleles or various combinations of wild-type and mutant alleles, can be employed simultaneously in a single amplification reaction. Amplification products can be distinguished by different labels or size (e.g., using gel electrophoresis).

A primer can be detectably labeled with a label that can be detected by spectroscopic, photochemical, biochemical, immunochemical or chemical means, for example (see, e.g., Sambrook, et al.). Useful labels include a dye, such as a fluorescent dye, a radioactive label, such as $^{32}P$, an electron-dense reagent, an enzyme, such as peroxidase or alkaline phosphatase, biotin, or haptens and proteins for which antisera or monoclonal antibodies are available.

A detectable oligonucleotide can be similarly labeled, such as with fluorescein. In this regard, if the primer is labeled with a dye and the detectable oligonucleotide is labeled with fluorescein and is designed to bind to the nascent strand opposite from the dye, fluorescence resonance energy transfer (FRET) across the DNA helix can occur. Other detectable oligonucleotides include a molecular probe, a TAQMAN® probe, a single-stranded DNA probe, a double-stranded DNA probe, and the like.

Nucleic acid amplification reagents include an enzyme having polymerase activity (e.g., AmpliTaq Gold®), one or more enzyme co-factors (e.g., $MgCl_2$), and deoxynucleotide triphosphates (dNTPs; e.g., dATP, dGTP, dCTP, and dTTP).

Conditions that promote amplification are those that promote annealing of primers and extension of nucleic acid sequences. Annealing is dependent on various parameters, such as temperature, ionic strength, length of sequences being amplified, complementarity, and G:C content of the sequences being amplified. For example, lowering the temperature promotes annealing of complementary nucleic acid sequences. High G:C content and longer length stabilize duplex formation. Generally, primers and detectable oligonucleotides of about 30 bp or less and having a high G:C content work well. Preferred amplification conditions, primers and detectable oligonucleotides are exemplified herein.

Amplification can be repeated any suitable number of times by thermal cycling the reaction mixture between about 10 and about 100 times, such as between about 20 and about 75 times, such as between about 25 and about 50 times.

Once the amplification reactions are completed, the presence of an amplified product can be detected using any suitable method. Such methods include, without limitation, those known in the art, such as gel electrophoresis with or without a fluorescent dye (depending on whether the product was amplified with a dye-labeled primer), a melting profile with an intercalating dye (see, e.g., PCR Technology, Principles, and Applications for DNA Amplification, Erlich, Ed., W. H. Freeman and Co., New York, 1992, Chapter 7), and hybridization with an internal detectable oligonucleotide. Other examples of methods include enzyme-linked immunosorbent assay (ELISA), electro-chemiluminescence, reverse dot blots, high pressure liquid chromatography (HPLC) (see, e.g., Lazar, Genome Res. 4: S1-S14 (1994)), and single-strand conformation polymorphism analysis of single-stranded PCR products also can be used (see, e.g., Orita, et al., PNAS USA 86: 2766-2770 (1989)).

Amplified nucleic acid can be detected by monitoring an increase in the total amount of double-stranded DNA (dsDNA) in the reaction mixture (see, e.g., U.S. Pat. No. 5,994,056 and European Pat. Pub. Nos. 487,218 and 512,334). A DNA-binding dye, such as SYBR Green, is used. The dye fluoresces when bound to dsDNA, and the increase in fluorescence is used to determine the increase in dsDNA.

Dideoxy sequencing-based methods and Pyrosequencing™ of oligonucleotide-length products also can be used to detect amplified nucleic acid. Another sequencing method is described by Kobayashi, et al., Mol. Cell. Detectable oligonucleotides 9: 175-182 (1995)).

When PCR is issued, detection can occur after amplification is complete, such as after using a labeled primer during amplification, by using a labeled primer as a detectable oligonucleotide after amplification, or by using a detectable oligonucleotide, which differs in sequence from the primers, after amplification to hybridize to the amplified target sequence. Labeled amplification products then can be separated and detected by other means.

Alternatively, the amplification and detection can be combined in a real-time PCR assay. When real-time PCR is used, the mixture can further comprise nucleic acid detection reagents, such as a non-specific fluorescent dye that intercalates with any double-stranded DNA, for example, or a sequence-specific DNA detectable oligonucleotide, which permits detection only after the detectable oligonucleotide hybridizes with its complementary DNA target, thereby enabling simultaneous amplification and detection. When a detectable oligonucleotide is present in the mixture during amplification, the detectable oligonucleotide should be stable under the conditions that promote amplification, should not interfere with amplification, should bind to its target sequence under amplification conditions, and emit a signal only upon binding its target sequence. Examples of detectable oligonucleotide that are particularly well-suited in this regard include molecular beacon detectable oligonucleotides, TAQMAN® detectable oligonucleotides, and linear detectable oligonucleotides, such as those described by Abravaya, et al. (U.S. Pat. App. Pub. No. 2005/0227257). The detectable oligonucleotides can form the loop region, alone or in further combination with part of the stem region, of a molecular beacon. The detectable oligonucleotides also can be used as linear detectable oligonucleotides with a fluorophore (e.g., FAM) at one end and a high-efficiency quencher, such as the Black Hole Quencher (BHQ®; BioSearch Technologies, Inc., Novato, Calif.), at the other end.

For exemplification only, approximately 1-2 microliters of the bisulfite-treated DNA can be used as a template for strand-specific PCR amplification in a region of interest. In a PCR reaction profile for amplifying a portion of the target sM9 sequence, for example, a procedure of initial denaturation of 94° C. for 3 minutes followed by a cycle of 94° C. of 30 seconds, 68° C. for 30 seconds, 72° C. for 30 seconds for a total of 30 cycles. The PCR reactions can be performed in 25 microliter volumes under conditions of: about 50 ng bisulfite-converted DNA (less for micro dissected samples), 10 mM Tris-HCl (pH 8.3), 1.5 mM $MgCl_2$, 50 mM KCl, 0.1% gelatin/ml, 100 µM of each of dNTP, 0.5 µM final concentration of each primer and 1 unit of Taq polymerase. There are many chromatographic techniques that can be used to isolate the PCR amplification products. In one illustrative procedure, approximately 10-25 microliters of the amplified PCR products were loaded onto 2% agarose gels and electrophoresed. The bands were visualized and isolated using standard get purification procedures.

Kits

Kits comprising compositions described herein or compositions made based on the invention described herein are contemplated. Such kits may include specific primers, probes and blockers, as necessary for performing the present invention with regard to any specific target nucleotide sequence.

Further, such kits are contemplated to have instructions, vials, solutions, markers, etc., as necessary to perform the present invention, or list any needed items. A kit of the present invention may include any and all of the primers, probes, blockers and other sequences as detailed below in the exemplification section. However, the kits of the present invention are not limited to these sequences as one of ordinary skill in the art can determine sequences necessary for the detection of target hyper and hypomethylated sequences based on the teachings of this specification.

In this regard, a kit can contain a container or a sample vial for storing a sample of a tissue or a body fluid. The primers, such as a pair of primers, specifically a forward primer and a reverse primer for both strands to be detected, can be in a composition in amounts effective to permit detection of mutant sequences. Detection of mutant sequences is accomplished using any of the methods described herein or known by one of ordinary skill in the art in the art for detecting a specific nucleic acid molecule in a sample. A kit can also comprise buffers, nucleotide bases and other compositions to be used in hybridization and/or amplification reactions.

The kit can further comprise dNTPs. Preferably, the dNTPs are supplied in a buffered solution with a reference dye.

The primers, detectable oligonucleotides and dNTPs can be packaged in various configurations. Preferably, the primers, detectable oligonucleotides and dNTPS are in a single container. The container preferably also contains a preservative, such as sodium azide and/or ProClin® 950.

The kit can further comprise a DNA polymerase, an RNA polymerase, a reverse transcriptase, and a mixture of two or more of the foregoing. Any suitable DNA polymerase can be used. An example of a preferred DNA polymerase is AmpliTaq Gold® (Life Technologies Corp., Carlsbad, Calif.). Likewise, any suitable RNA polymerase can be used. An example of a preferred reverse transcriptase-DNA polymerase is rTth. The polymerase can be supplied in a buffered solution, which optionally contains, and preferably does contain, stabilizers.

The kit can further comprise an activation reagent, such as magnesium chloride, in a buffered solution. The buffered solution preferably includes a preservative, such as sodium azide and/or ProClin® 950.

The kit can optionally further comprise an IC. The IC is an unrelated DNA sequence that demonstrates that the process has proceeded correctly for each sample. Any suitable sequence can be used as the IC. Examples of IC target sequences include those set forth in the EXAMPLES herein. The target-specific detectable oligonucleotides and the IC-specific detectable oligonucleotides are labeled differently so that target DNA and IC DNA can be distinguished. An example of a label for the IC-specific detectable oligonucleotide is Cy5. Preferably, the label Cy5 is used in combination with the quencher BHQ-2.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under herein and are otherwise defined, described, or discussed elsewhere in the "Detailed Description" or elsewhere in this specification, all such definitions, descriptions and discussions are intended to be attributed to such terms. There also is no intention in the use of such terms and expressions of excluding any equivalents of the features shown and described or portions thereof.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as defined by the appended claims.

EXEMPLIFICATION

Example 1

This example provides support for the present invention with regard to the utilization of primers, probes and other oligonucleotides such as blockers for the improved detection of target nucleotide sequences that have been the subject of bisulfite conversion procedures.

FIG. 1 shows the sequences for original and complementary sequences before and after bisulfite treatment. The complementarity of the two strands is lost after treatment. Bolded, underlined "C" is methylated cytosine.

The current mS9 oligo primer designs as are known in the art are show on Table 1, below.

TABLE 1

The current mS9 oligo designs are detailed in table below (see, e.g., Warren, et al., BMC Medicine, 2011, 9:133.)

| Oligo | Sequence 5'-->3' | Tm |
|---|---|---|
| Forward Primer | GATTXGTTGTTTATTAGTTATTATGT [SEQ ID NO: 1] | 60.2 |
| Reverse Primer | AAATAATCCCATCCAACT [SEQ ID NO: 2] | 61.8 |
| blocker | GTTATTATGTTGGATTTTGTGGTTAATGTGTAG (blocker) [SEQ ID NO: 3] | 73.4 |
| Probe | TTAACCGCGAAATCCGAC [SEQ ID NO: 4] | 67.4 |

Note:
Tm is calculated using Vector NTI software. The non-nucleic acid labels were not considered in the Tm calculation. "X" in the Forward primer sequence indicates the abasic site.

New designs for the same DNA strand as above in Table 1 (original) are detailed in Table 2, below.

TABLE 2

| Oligo | Sequence 5'-->3' | Tm |
|---|---|---|
| Block for the RP | TCCAACTACACATTAACCACAAAATCC (blocker) [SEQ ID NO: 5] | 73.7 |

TABLE 2-continued

| Oligo | Sequence 5'-->3' | Tm |
|---|---|---|
| Block for the RP-2 | CATCCAACTACACATTAACCACAAAATC (blocker) [SEQ ID NO: 6] | 73.2 |
| PNA blocker for FP (UN-PNA4) | TATGTTGGATTTTGTGG [SEQ ID NO: 7] | 62 |
| PNA blocker for RP (UN-PNA3) | CCAACTACACATTAACC [SEQ ID NO: 8] | 64 |
| New Probe Original Strand (FAM) | CGGATTTCGCGGTTAACG (BHQ1-dT) [SEQ ID NO: 9] | 70.2 |

Note:
Tms for the 2 PNA blockers were calculated per Nucleic Acids Symp Ser (Oxf). 2004; (48):131-2.

One consequence of bisulfite conversion in mS9 assay procedure is that the double-stranded conformation of the original target is disrupted due to loss of sequence complementarity. The target sequences exist as two separate single-stranded DNAs during sample preparation and the analytical testing. Further, circulating mS9 sequences may also exist at very low concentrations. Contrary to accepted practice in the art, It was conceived that it would be advantageous that the assay detect both DNA strands (original and complement strands) as a result of bisulfite treatment. This would improve assay sensitivity. The new designs for the complement strand in this exemplification are given in Table 3, below.

TABLE 3

| Oligo | Sequence 5'-->3' (for DNA) or N'-->C' (for PNA) | Tm |
|---|---|---|
| comp FP full | AAAuGAuTTuAuuTAGTTG [SEQ ID NO: 10] | 62.7 |
| comp RP far | CTACCCACCAACCATC [SEQ ID NO: 11] | 62.7 |
| comp RP near | CCACCAACCATCATATC [SEQ ID NO: 12] | 62 |
| comp Probe on FP strand short | (FAM) TTGATCGCGGGGTTCG (BHQ1-dT) [SEQ ID NO: 13] | 70.8 |
| comp Probe on FP strand shorter | (FAM) CGCGTTGATCGCGGG (BHQ1-dT) [SEQ ID NO: 14] | 72.8 |
| comp Probe on RP strand-1 | (FAM) AACCCGCGATCAACG (BHQ1-dT) [SEQ ID NO: 15] | 69.6 |
| comp Probe on RP strand-2 | (FAM) CCGCGATCAACGCGC (BHQ1-dT) [SEQ ID NO: 16] | 73 |
| blocker RP overlap | CATATCAAACCCCACAATCAACACA (3SpC3) [SEQ ID NO: 17] | 75.7 |
| blocker FP overlap | TTTAGTTGTGTGTTGATTGTGGGGTT (3SpC3) [SEQ ID NO: 18] | 75.3 |
| PNA blocker for FP (UN-PNA2) | GTTGTGTGTTGATTGTG [SEQ ID NO: 19] | 64 |
| PNA blocker for RP (UN-PNA1) | CATCATATCAAACCCCA [SEQ ID NO: 20] | 64 |
| MGB blocker for RP-1 | (MGB) AAACCCCACAATCAACACAC AACTAAA [SEQ ID NO: 21] | 78.1 |
| MGB blocker for RP-2 | (MGB) AAACCCCACAATCAACACAC AAC [SEQ ID NO: 22] | 74.8 |
| MGB blocker for RP-2 | (MGB) AAACCCCACAATCAACACAC AA [SEQ ID NO: 23] | 72.1 |
| MGB blocker for FP-1 | (MGB) TGTGTTGATTGTGGGGTTTG ATATGA [SEQ ID NO: 24] | 75.7 |
| MGB blocker for FP-2 | (MGB) TGTGTTGATTGTGGGGTTTG ATATG [SEQ ID NO: 25] | 74.4 |
| MGB blocker for FP-3 | (MGB) TGTGTTGATTGTGGGGTTTG ATAT [SEQ ID NO: 27] | 73.2 |

Note:
For comp FP full, "T"s in the original sequence were replaced with 5-Propynyl dU ("u"). The original Tm was 54.2 (using vector NTI and assumptions as mentioned above). Each T-->u modification increased Tm by 1.7 degree Celsius (per http://www.glenresearch.com/GlenReports/GR17-12.html).
Note:
Tms for the 2 PNA blockers were calculated per Nucleic Acids Symp Ser (Oxf). 2004; (48):131-2.
Note:
Tms for the MGB blockers were calculated using Primer Express 2.0.

Target mS9 sequences were subject to bisulfite treatment by methods known to those of skill in the art. The resulting converted sequences were subject to PCR using the probes given above. The control was using probes for the detection of one strand, as is standard in the art. The results of the experiment are given below.

The data presented in Table 4, below, shows that the method of the present invention wherein both strands of the bisulfite converted target nucleotide sequence of mS9 are detected results in vastly improved detection of the target sequence over the prior art method of only detected a single strand of the bisulfite converted mS9 target nucleotide sequence.

TABLE 4

| | % Detection of PCR replicates |
|---|---|
| Single strand detected | 200/447 = 45% |
| Two strands detected | 258/445 = 58% |

What is claimed is:
1. A composition comprising the primer SEQ ID NO: 10.
2. The composition of claim 1, wherein said primer is labeled.

\* \* \* \* \*